US011617566B2

(12) United States Patent
Jin et al.

(10) Patent No.: US 11,617,566 B2
(45) Date of Patent: Apr. 4, 2023

(54) ULTRASONIC IMAGING DEVICE AND IMAGING METHOD THEREOF

(71) Applicant: GE Precision Healthcare LLC, Wauwatosa, WI (US)

(72) Inventors: Lu Jin, Jiangsu (CN); Bing Li, Jiangsu (CN); Qiang Yao, Jiangsu (CN); Liping Chen, Jiangsu (CN); Lanping Liu, Jiangsu (CN); Kejian Shi, Jiangsu (CN)

(73) Assignee: GE Precision Healthcare LLC, Wauwatosa, WI (US)

(*) Notice: Subject to any disclaimer, the term of this patent is extended or adjusted under 35 U.S.C. 154(b) by 264 days.

(21) Appl. No.: 17/112,424

(22) Filed: Dec. 4, 2020

(65) Prior Publication Data

US 2021/0169451 A1 Jun. 10, 2021

(30) Foreign Application Priority Data

Dec. 6, 2019 (CN) .......................... 201911241071.X

(51) Int. Cl.
*A61B 8/00* (2006.01)
*G01S 15/89* (2006.01)
*A61B 8/08* (2006.01)

(52) U.S. Cl.
CPC ............ *A61B 8/463* (2013.01); *A61B 8/0858* (2013.01); *G01S 15/89* (2013.01)

(58) Field of Classification Search
None
See application file for complete search history.

(56) References Cited

U.S. PATENT DOCUMENTS

| 7,837,674 B2* | 11/2010 | Cooper ................. A61B 34/37 606/1 |
| 9,131,919 B2 | 9/2015 | Summers |
| 2010/0174185 A1 | 7/2010 | Wang |
| 2014/0121520 A1 | 5/2014 | Wang |
| 2015/0094588 A1* | 4/2015 | Summers ............ A61B 8/0825 600/445 |
| 2017/0189128 A1* | 7/2017 | Auld ...................... A61B 34/30 |

FOREIGN PATENT DOCUMENTS

| CN | 104095657 A | 10/2014 |
| CN | 208511054 U | 2/2019 |

* cited by examiner

*Primary Examiner* — Jonathan Cwern

(57) ABSTRACT

The present invention provides an ultrasonic imaging device, comprising: an imaging assembly, the imaging assembly comprising an ultrasonic transducer for imaging tissue to be imaged; an adjustable arm, wherein one end of the adjustable arm is connected to the imaging assembly; a counterweight, the counterweight being connected to the other end of the adjustable arm through a cable; a frame, the frame being capable of guiding movement when the counterweight and/or adjustable arm moves; and a transmission assembly, the transmission assembly comprising a driving device and a transmission belt, wherein the driving device is connected to the transmission belt, and the transmission belt is connected to the counterweight; the driving device is capable of acting on the counterweight through the transmission belt, so as to adjust pressure applied by the imaging assembly onto the tissue to be imaged. The present invention further provides some imaging methods using the ultrasonic imaging device.

17 Claims, 7 Drawing Sheets

ULTRASONIC IMAGING DEVICE AND IMAGING METHOD THEREOF

CROSS-REFERENCE TO RELATED APPLICATIONS

This application claims the benefit of Chinese Patent Application No. 201911241071.X filed on Dec. 6, 2019, the disclosure of which is herein incorporated by reference in its entirety.

TECHNICAL FIELD

The subject matter disclosed in the present invention relates to the field of medical imaging, and particularly, to an ultrasonic imaging device and an imaging method using the device.

BACKGROUND

Common medical imaging devices include ultrasonic imaging devices, magnetic resonance imaging devices, X-ray imaging devices, and the like. Among these devices, ultrasonic imaging devices have the advantages of real-time imaging, minimal risks, low costs, and the like. A breast ultrasonic scanning device is one of the ultrasonic imaging devices, and generates breast images through echo signals of high-frequency sound waves emitted by a detector in an imaging assembly. Breast ultrasonic scanning can be used as a supplementary means of breast cancer screening.

In an example, the breast ultrasonic scanning device may be used to image breast tissue in one or a plurality of planes. In some breast ultrasonic scanning devices, a person to be scanned may receive the scan in supine position or other positions. Before initiating a scan, a user of a scanning device places an imaging assembly onto tissue of a person to be scanned and applies to the imaging assembly a force downward relative to the breast, so as to press the tissue and correctly image the tissue. At this time, positioning the scanning device and adjusting the pressure applied by the imaging assembly are crucial.

SUMMARY

Some embodiments of the present invention provide an ultrasonic imaging device, comprising: an imaging assembly, the imaging assembly comprising an ultrasonic transducer for imaging tissue to be imaged; an adjustable arm, wherein one end of the adjustable arm is connected to the imaging assembly; a counterweight, the counterweight being connected to the other end of the adjustable arm through a cable; a frame, the frame being capable of guiding movement when the counterweight and/or adjustable arm moves; and a transmission assembly, the transmission assembly comprising a driving device and a transmission belt, wherein the driving device is connected to the transmission belt, and the transmission belt is connected to the counterweight; the driving device is capable of acting on the counterweight through the transmission belt, so as to adjust pressure applied by the imaging assembly onto the tissue to be imaged.

Optionally, the device further comprises a first pulley block, wherein the first pulley block comprises a number of pulleys disposed on the frame and the other end of the adjustable arm; the cable is wound through the pulley block and has two ends disposed on the counterweight.

Optionally, the frame comprises a number of pillar structures, and the counterweight is provided with through-holes for the pillar structures to pass through; the pillar structures are usable for guiding movement during movement of the counterweight.

Optionally, the frame comprises a hollow structure, and at least part of the adjustable arm is disposed in the hollow structure; the hollow structure is usable for guiding movement during movement of the adjustable arm.

Optionally, the driving device comprises a motor assembly and a clutch, the motor assembly is connected to the clutch, and the clutch is connected to the transmission belt.

Optionally, the motor assembly comprises a motor and a reducer; an output shaft of the motor comprises a worm structure; the reducer comprises a worm gear mated with the worm structure; the worm is mated with the worm gear to enable automatic locking of a position of the counterweight in an OFF state of the motor.

Optionally, the clutch is connected to the transmission belt through a driving wheel.

Optionally, one side of the transmission belt is connected to the counterweight to drive the counterweight to move.

Optionally, the device further comprises a driven wheel, wherein the driven wheel is disposed on the frame and connected to the transmission belt.

Optionally, the driving wheel comprises a gear structure, and a portion of the transmission belt in contact with the driving wheel has a tooth-like structure that is engaged with the gear structure.

Optionally, the device further comprises a tensioning device, wherein the tensioning device comprises a movable tensioning wheel; the movable tensioning wheel is disposed on the frame and movably attached to the transmission belt through a torsion spring.

Optionally, the tensioning device further comprises a fixed tensioning wheel, and the fixed tensioning wheel is disposed opposite to the movable tensioning wheel and attached to the transmission belt.

Optionally, the device further comprises a driven wheel adjusting device, wherein the driven wheel is disposed on the frame by means of the driven wheel adjusting device; the driven wheel adjusting device comprises a fixing seat and an adjusting rod; the driven wheel is disposed on the fixing seat; the adjusting rod is threadedly connected to the fixing seat and the frame, so that a position of the driven wheel is capable of being adjusted by rotating the adjusting rod.

Optionally, the driven wheel adjusting device further comprises a guide rod, one end of the guide rod is disposed on the frame, and the other end passes through the fixing seat.

Optionally, the clutch comprises an electromagnetic clutch body, a base, an adapter, a support bearing, a bearing seat, and a driving wheel; the electromagnetic clutch body is disposed on the base and connected to the adapter; the adapter is rotatably connected to the support bearing and is connected to the driving wheel through a rotating shaft; the support bearing is disposed on the bearing seat; the driving wheel is connected to the transmission belt.

Optionally, the device further comprises a second pulley block disposed on the frame and a third pulley block disposed on the counterweight; the second pulley block is used for sliding connection between the frame and the adjustable arm; the third pulley block is used for sliding connection between the frame and the counterweight.

Some other embodiments of the present invention provide an imaging method, comprising: adjusting a position of an imaging assembly so that the imaging assembly is close to a surface of tissue to be imaged; controlling the driving device to act on the counterweight, and adjusting pressure applied by the imaging assembly onto the tissue to be imaged; and using the imaging assembly to perform imaging.

Optionally, when the position of the imaging assembly is adjusted, the clutch in the driving device is in a disengaged state; at this time, the position of the imaging assembly is adjusted manually.

Optionally, when the driving device acts on the counterweight, the clutch in the driving device is in an engaged state; at this time, the driving device is capable of acting on the counterweight to change a force applied by the counterweight to the adjustable arm, thereby changing a force applied to the imaging assembly.

It should be understood that the brief description above is provided to introduce in simplified form some concepts that will be further described in the Detailed Description of the Embodiments. The brief description above is not meant to identify key or essential features of the claimed subject matter. The scope is defined uniquely by the claims that follow the detailed description. Furthermore, the claimed subject matter is not limited to implementations that solve any disadvantages noted above or in any section of the present disclosure.

DETAILED DESCRIPTION OF THE EMBODIMENTS

Specific implementation manners of the present invention will be described in the following. It should be noted that during the specific description of the implementation manners, it is impossible to describe all features of the actual implementation manners in detail in the present invention for the sake of brief description. It should be understood that in the actual implementation of any of the implementation manners, as in the process of any engineering project or design project, a variety of specific decisions are often made in order to achieve the developer's specific objectives and meet system-related or business-related restrictions, which will vary from one implementation manner to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art. "First," "second" and similar words used in the present invention and the claims do not denote any order, quantity or importance, but are merely intended to distinguish between different constituents. "One," "a(n)" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

Although some embodiments of the present invention are presented in the particular context of human breast ultrasound, it should be understood that the present invention is applicable to ultrasonic scanning of any externally accessible human or animal body part (for example, abdomen, legs, feet, arms, or neck), and is also applicable to other medical imaging devices (for example, X-ray scanning) with a similar mechanical structure. Moreover, although some embodiments of the present invention are presented in the particular context of mechanized scanning, it should be understood that the present invention is also applicable to a handheld scanning context.

Figure 1:
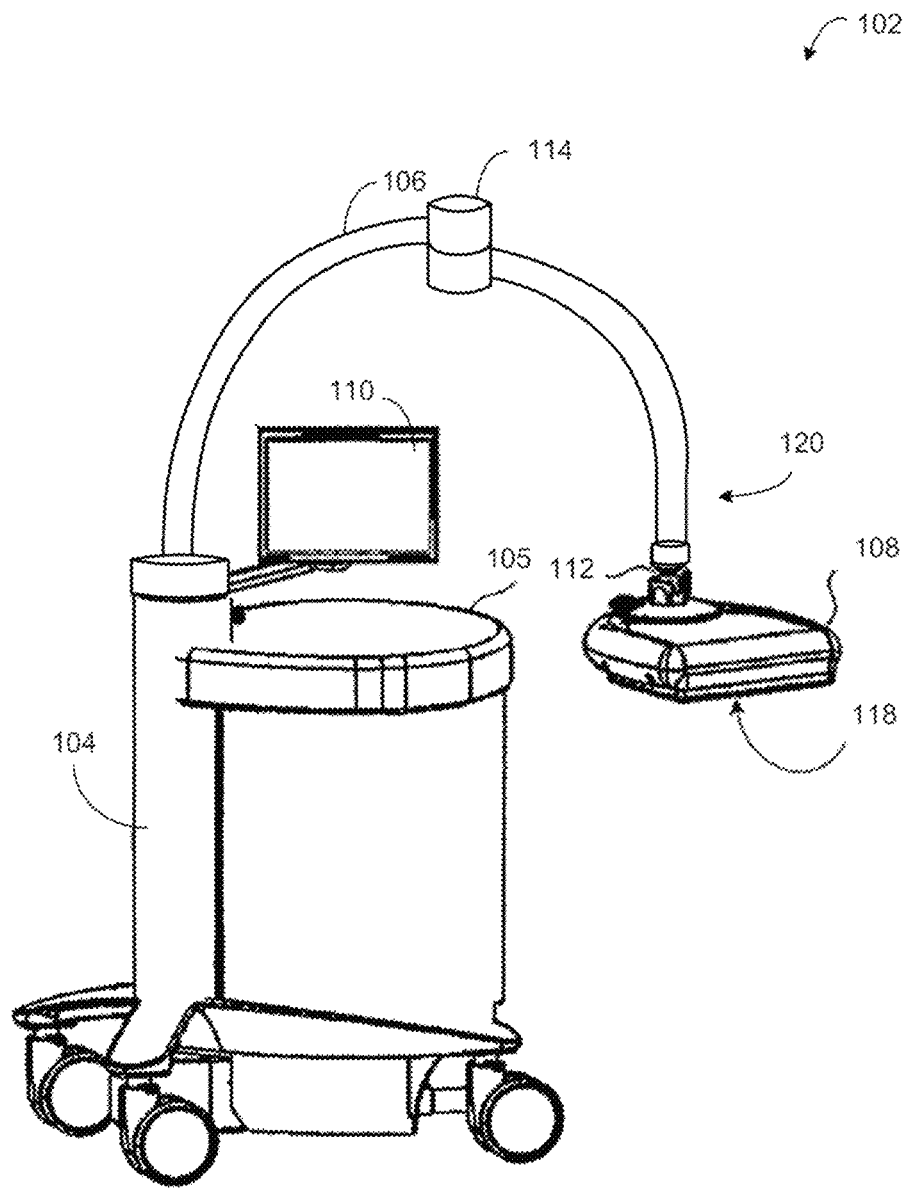
FIG. 1 is a schematic structural view of a breast ultrasonic scanning device according to some embodiments of the present invention.

Referring to FIG. 1, a perspective view of a breast ultrasonic scanning device 102 (hereinafter also referred to as a scanning device 102) according to some embodiments of the present invention is shown. The scanning device 102 includes a frame 104, an ultrasonic processor housing 105 including an ultrasonic processor, an adjustable arm 106 including a hinge joint 114, an imaging assembly 108 connected to one end 120 of the adjustable arm 106 through a ball joint 112, and a display 110 connected to the frame 104. The imaging assembly 108 includes an ultrasonic transducer. The display 110 may be connected to the frame 104 at an interface where the adjustable arm 106 enters the frame 104. Since the display 110 is directly connected to the frame 104 rather than the adjustable arm 106, the display 110 does not affect the weight of the adjustable arm 106 and the balancing mechanism of the adjustable arm 106. In some embodiments, the display 110 may be rotated in a horizontal and transverse direction (for example, rotatable about a central axis of the frame 104), but not vertically. In some other embodiments, the display 110 may also be vertically movable.

It should be noted that FIG. 1 merely illustrates, as a reference, some configuration manners and relative positions of various components, but these configuration manners and relative positions are not unique. For example, the position of the display 110 is arbitrary. The display 110 may, for instance, be disposed on the ultrasonic processor housing 105, or may be arbitrarily disposed independently of the frame 104 or the housing 105. The shape of the adjustable arm 106 is not necessarily curved like in FIG. 1, the adjustable arm 106 may also have a polyline shaped structure or even straight line shaped structure, and the adjustable arm 106 may also not include the hinge joint 114 but be integrally formed or have any other type of configuration without affecting the implementation of various embodiments of the present invention. In addition, the arrangement of the ball joint 112 is not the only possible arrangement. Other types of connection may also be selected to connect the adjustable arm 106 and the imaging assembly 108. In some embodiments, the imaging assembly 108 includes a film 118 that is in a substantially tensioned state to be at least partially attached, for pressing the breast. The film 118 has a bottom surface in contact with the breast, and meanwhile the transducer sweeps over a top surface of the film 118 to scan the breast. The film 118 may be a tensioned fabric sheet.

In some embodiments, the adjustable arm 106 is configured such that the imaging assembly 108 has a net downward weight of substantially zero or has a small net downward weight (for example, 1 to 2 Kg). With such net downward weight, the position of the imaging assembly 108 can be arbitrary adjusted by a user and the imaging assembly 108 can remain stationary after adjustment. In some other embodiments, after the imaging assembly 108 is brought into contact with tissue to be scanned by the adjustment, the internal components of the scanning device 102 may be adjusted to apply a desired downward weight to press the breast and improve imaging quality. In some embodiments, the net downward weight may be in the range of 2 to 11 Kg. The weight adjustment of the imaging assembly 108 will be described in detail below.

Figure 2:
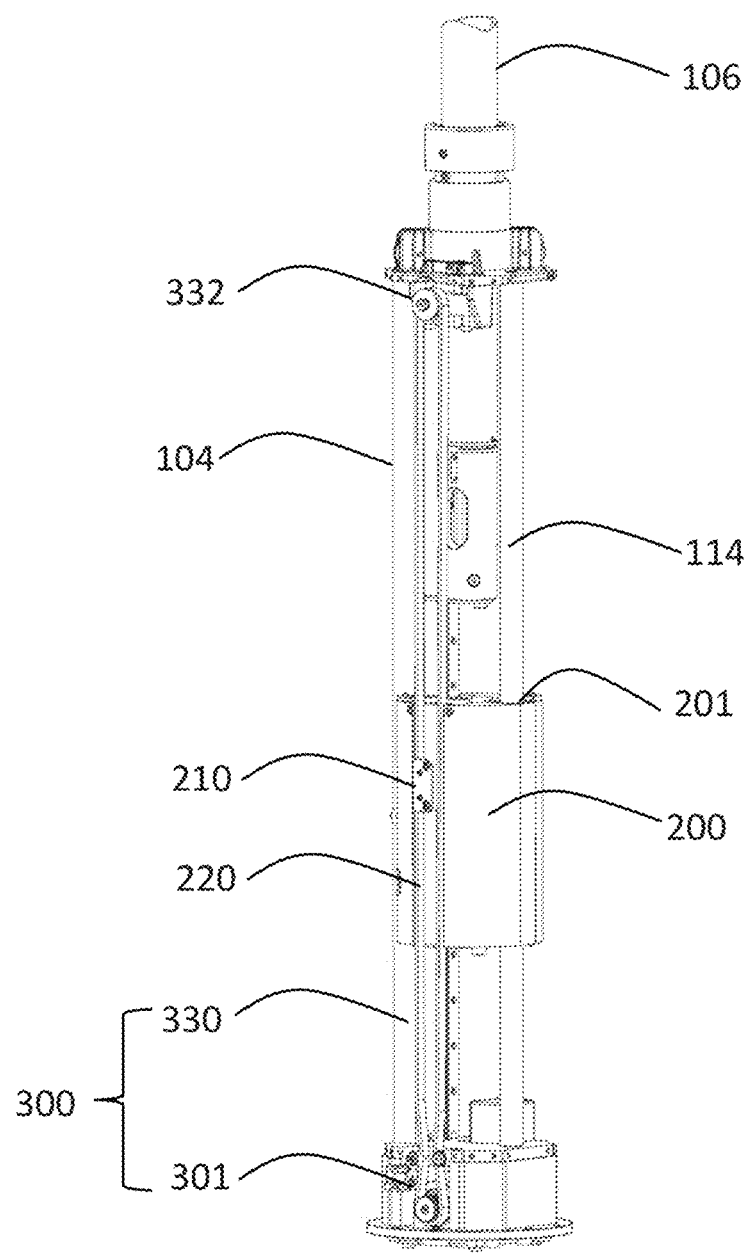
FIG. 2 is a schematic view illustrating a connection relationship between a transmission assembly and a counterweight according to some embodiments of the present invention.
Figures 3, 4:
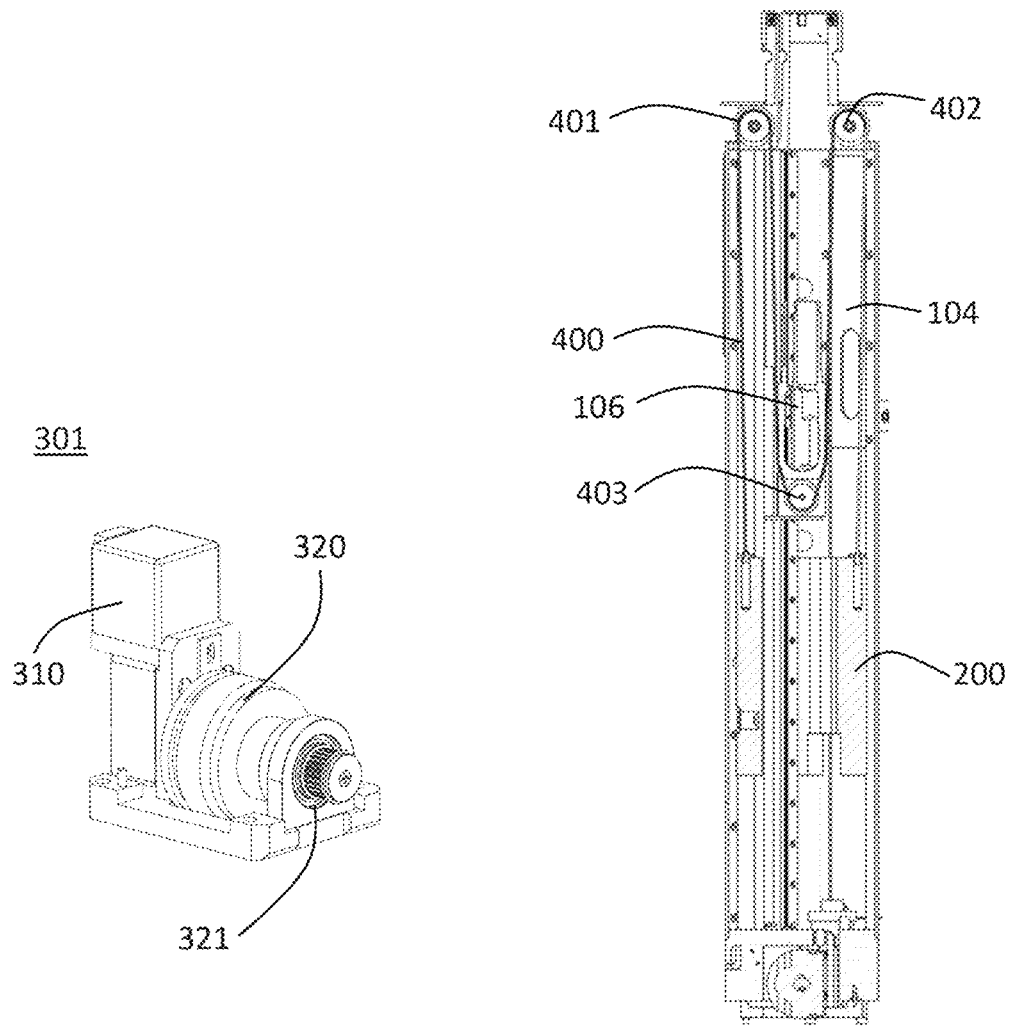
FIG. 3 is a schematic structural view of a driving device in the transmission assembly according to some embodiments of the present invention.
FIG. 4 is a schematic view illustrating a connection relationship between the counterweight and an adjustable arm according to some embodiments of the present invention.

Referring to FIGS. 2 to 4, schematic views illustrating connection relationships between the adjustable arm 106 and a counterweight 200 as well as a transmission assembly 300 in some embodiments of the present invention are shown. Referring first to FIG. 2, a schematic view illustrating a connection relationship between the transmission assembly 300 and the counterweight 200 in some embodiments of the present invention is shown. The frame 104 includes a hollow structure, where at least part of the adjustable arm 106 is disposed in the hollow structure, and the frame 104 can guide movement when the adjustable arm moves along the hollow structure. It should be noted that the hollow structure may come in any form, such as a circle matching the shape of the adjustable arm 106, or any other shape. In addition, the frame 104 may further include a number of pillar structures 114, and accordingly, through-holes 201 are provided in the counterweight 200. The pillar structure 114 matches the through-hole 201 in the counterweight 200 and can pass through the through-hole 201. The matching between the pillar structure 114 and the through-hole 201 can be used for guiding movement during movement of the counterweight 200, and can avoid cable winding or knotting caused by swinging of the counterweight 200 during movement. In addition to the arrangement of the pillar structure 114 and the through-hole 201 matching each other, any other manners of fixing the counterweight 200 are also allowed, and will not be exhausted herein. Furthermore, although the frame 104 shown in FIG. 2 does not include a housing, those skilled in the art should know that the housing structure shown in FIG. 1 may be disposed outside the frame 104 in the actual arrangement. FIG. 2 further shows a schematic view illustrating a connection relationship between the transmission assembly 300 and the counterweight 200. The transmission assembly 300 includes a driving device 301 and a transmission belt 330. The driving device 301 is connected to the transmission belt 330, and the transmission belt 330 is connected to the counterweight 200, so as to achieve transmission between the transmission assembly 300 and the counterweight.

In some embodiments, the counterweight 200 may be provided with a fixing device 210, where the fixing device 210 may be connected to one side of the transmission belt 330, so as to achieve connection between one side of the transmission belt 330 and the counterweight 200. Such arrangement enables the transmission belt 330 to drive the counterweight 200 to move. In addition, the counterweight 200 may further be provided with a notch 220 matching the transmission belt 330. The notch 220 can accommodate the transmission belt 330, so that the transmission belt 330 does not contact the counterweight 200 and produce wear when the transmission belt 330 transmits the counterweight 200. Meanwhile, such arrangement enables the transmission belt 330 and the counterweight 200 to be more compactly arranged. It should be noted that although the transmission belt 330 is a belt structure in some embodiments, some other configuration manners of the transmission belt are also allowed, for example, a chain structure or a rack structure. Although FIG. 2 shows that a driving wheel 321 is at the bottom of the frame, and a driven wheel 332 is at the top of the frame, the positional relationship between them can also be adjusted.

Referring now to FIG. 3, FIG. 3 is a schematic structural view of the driving device 301 in the transmission assembly 300 in some embodiments of the present invention. The driving device 301 includes a motor assembly 310 and a clutch 320, and the motor assembly 310 is connected to the transmission belt 330 through the clutch 320. In some embodiments, the clutch 320 is provided with a driving wheel 321, where the driving wheel 321 may be connected to one end of the transmission belt 330 as in FIG. 2. The other end of the transmission belt 330 may be connected to the driven wheel 332. The driven wheel 332 may be disposed on the frame 104, and the distance between the driven wheel 332 and the driving wheel 321 may be set to be approximately equal to the length of the transmission belt 330 after being tensioned, so as to achieve close fit between the transmission belt 330 and the driving wheel 321, thereby enabling transmission under the driving of the driving wheel 321.

Referring to FIG. 4 in the following, FIG. 4 is a schematic view illustrating a connection relationship between the counterweight 200 and the adjustable arm 106 in some embodiments of the present invention. The frame 104 is provided with a first pulley 401 and a second pulley 402. A third pulley 403 is disposed at the bottom of the adjustable arm 106. The first, second, and third pulleys together form a first pulley block to guide movement of a cable 400. The cable 400 is wound through the pulley block formed by the first pulley 401, the third pulley 403, and the second pulley 402. Two ends of the cable 400 may be disposed on the counterweight 200 respectively. In some embodiments, the plane formed by connecting lines of the pulley block constituted by the three pulleys can approximately coincide with a central axis of the adjustable arm. Such arrangement ensures more smooth movement of the counterweight 200 and the adjustable arm 106 under the guidance of the frame 104. In some embodiments, the weight of the counterweight 200 is approximately equal to the sum of the weights of the adjustable arm 106 and the imaging assembly 108. Such arrangement ensures that when the clutch 320 is in a disengaged state, the imaging assembly 108 has a net downward force approximately equal to zero and can substantially keep force balance. At this time, an operator only needs to apply a small force to the adjustable arm 106 or the imaging assembly 108 to change the position of the imaging assembly 108, and when the force is removed, the imaging assembly 108 can reach a stationary state rapidly. It should be noted that the number of the pulley blocks described above is not fixed, and those skilled in the art can appropriately increase or decrease the number according to needs under the teachings of the present invention. Or, the pulley block can be replaced with other structures capable of guiding movement of the cable 404, for example, a sliding block.

During use of the device of the present invention, the motor assembly 310 may not perform power output on the transmission belt 330 when the clutch 320 is in the disengaged state. At this time, the transmission belt 330 has small resistance only to the counterweight 200, and the operator can manually control the adjustable arm 106 or the imaging assembly 108 to conveniently adjust the position of the imaging assembly 108. For example, the imaging assembly 108 may be brought close to tissue to be imaged by having a downward force applied to the adjustable arm 106 or the imaging assembly 108. When the motor assembly 310 and the clutch 320 are in an ON state, the transmission assembly 300 can transmit the counterweight 200 by means of the transmission belt 330. In some embodiments, the counterweight 200 may be subjected to a force applied by the transmission belt 330 that is upward relative to the bottom of the frame 104. At this time, the force applied by the counterweight 200 to the bottom of the adjustable arm 104 through the cable 400 will be decreased, and the pressure applied by the imaging assembly 108 onto the surface of the tissue to be imaged will be increased. In some embodiments, the counterweight 200 may also be subjected to a force applied by the transmission belt 330 that is downward relative to the bottom of the frame 104. At this time, the force applied by the counterweight 200 to the bottom of the adjustable arm 104 through the cable 400 will be increased, and accordingly, the pressure applied by the imaging assembly 108 onto the surface of the tissue to be imaged will be decreased. To sum up, when the clutch 320 is in the engaged state, the motor assembly 310 can drive the counterweight 200 to move through the transmission belt 330, so as to adjust the pressure applied by the imaging assembly 108 onto the tissue to be imaged. Since the counterweight 200 of the present invention may be an integral structure, no other complex pressure adjusting device is needed, and the pressure on the imaged tissue can be adjusted just by means of the transmission of the entire counterweight by the motor assembly 310, the clutch 320, and the transmission belt 330, which reduces to a great extent the complexity of device setup and the complexity of operation. In addition, the integrally-formed counterweight 200 also has a high degree of durability.

Figure 5:
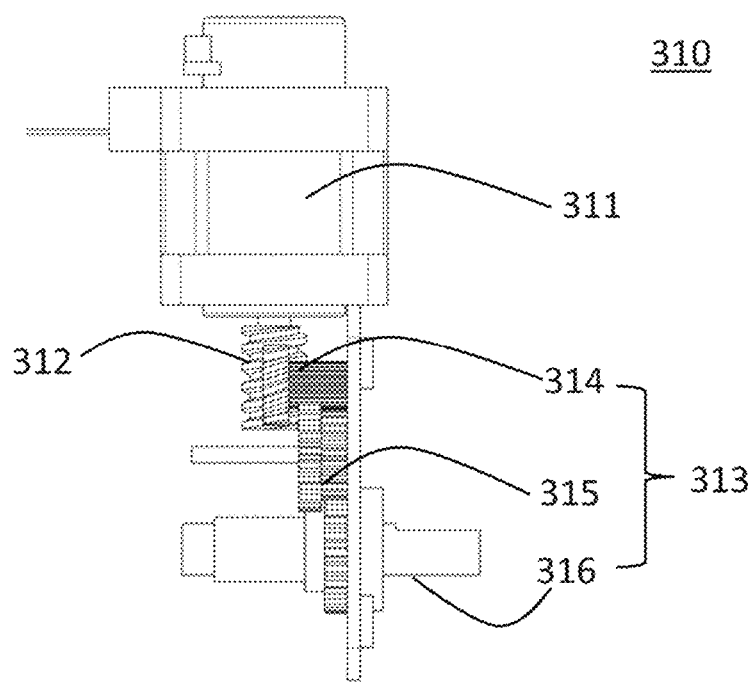
FIG. 5 is a schematic view illustrating an internal structure of the driving device according to some embodiments of the present invention.

The imaging assembly 107 may need to maintain stable pressure on the tissue to be imaged in the imaging process. At this time, the position of the imaging assembly 107 needs to be locked. The implementation of the locking function usually requires a complex design. A simplified technical solution for locking the imaging assembly 107 is provided in some embodiments of the present invention. As shown in FIG. 5, a schematic view illustrating an internal structure of the driving device 301 in some embodiments of the present invention is shown. The driving device 301 includes a motor assembly 310, where the motor assembly 310 may include a motor 311 and a reducer 313 connected to the motor 311. An output shaft of the motor 311 includes a worm structure 312. The reducer 313 includes a worm gear 314 mated with the worm structure 312, where the worm gear 314 is connected to a reducer output shaft 316 through a reducer gear set 315, so as to achieve power output of the motor assembly. Since the transmission between the worm gear and the worm has a reverse self-locking function, after the motor 311 stops rotating, the worm 312 can lock the worm gear 314, so as to achieve locking of the reducer output shaft 316. When the pressure applied by the imaging assembly 108 onto the tissue to be imaged is adjusted to an expected value, the output shaft of the motor 311 may stop rotating (for example, the power is cut off). At this time, the position of the counterweight 200 can be automatically locked, thereby achieving locking of the pressure applied by the imaging assembly 108 onto the tissue to be imaged. Such arrangement avoids the arrangement of an additional locking device and reduces the complexity of device setup to a great extent while maintaining the function of locking the imaging assembly 108.

Figure 6:
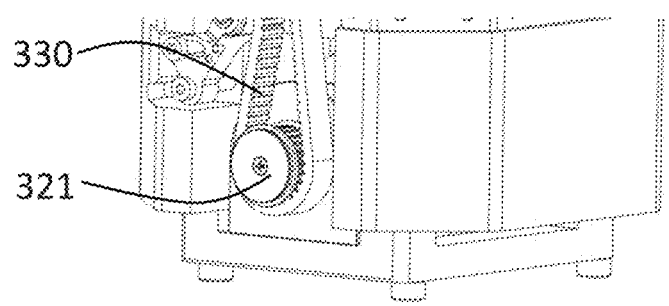
FIG. 6 is a partial view of a portion of a driving wheel in contact with a transmission belt according to some embodiments of the present invention.

As described above, the adjustment of the pressure applied by the imaging assembly 108 onto the tissue to be imaged has a very important impact on the imaging quality. In some embodiments of the present invention, the adjustment of the pressure applied by the imaging assembly 108 onto the tissue to be imaged relies on the transmission of the transmission assembly 300. Therefore, it is very important to ensure precise transmission of the transmission assembly 300. As shown in FIG. 6, a partial view of a portion of the driving wheel 321 in contact with the transmission belt 330 in some embodiments of the present invention is shown. The driving wheel 321 may include a gear structure. The gear structure may cover the entire periphery of the driving wheel 321 as in FIG. 6, or may be of other configuration types, for example, partially covering the driving wheel 321. Accordingly, a portion of the transmission assembly 300 in contact with the driving wheel 321 has a tooth-like structure engaged with the aforementioned gear. Such arrangement ensures that unexpected slip does not occur when the driving wheel 321 performs power output on the transmission belt 330. Moreover, in performing the locking function described above, the engaged tooth-like structure can also avoid slipping of the transmission belt 330, thereby ensuring reliability of the imaging device.

Figure 7:
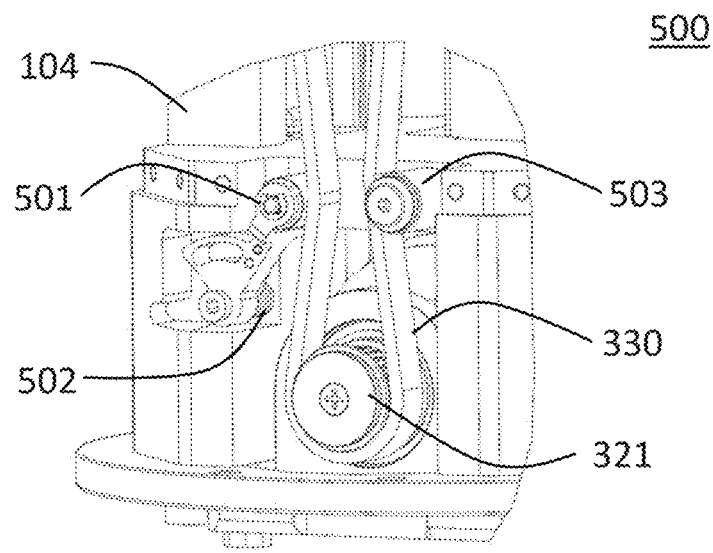
FIG. 7 is a schematic structural view of a tensioning device according to some embodiments of the present invention.

As shown in FIG. 7, a schematic structural view of a tensioning device 500 in some embodiments of the present invention is shown. The tensioning device 500 may include a movable tensioning wheel 501, where the movable tensioning wheel 501 may be disposed on the frame 104 in an appropriate manner, for example, mounted on the frame 104 by means of a mounting shaft. The movable tensioning wheel 501 may also be movably attached to the transmission belt 330 through a torsion spring 502. Such manner ensures that the movable tensioning wheel 501 is closely attached to the transmission belt 330, thereby ensuring tight connection between the transmission belt 330 and the driving wheel 321. A portion of the movable tensioning wheel 501 attached to the transmission belt 330 may be configured as a rotating structure, for example, a roller structure, so that the friction between the transmission belt 330 and the movable tensioning wheel 501 can be reduced during movement of the transmission belt 330, thereby avoiding unexpected wear. In addition, the tensioning device 500 may further include a fixed tensioning wheel 503, where the fixed tensioning wheel 503 may be configured to be closely attached to the transmission belt 330. In some embodiments, the fixed tensioning wheel 503 may be disposed on the other side opposite to the movable tensioning wheel 501 as in FIG. 7, disposed opposite to the movable tensioning wheel 501 and attached to the transmission belt 330, so as to be better used in combination with the movable tensioning wheel 501. A portion of the fixed tensioning wheel 503 attached to the transmission belt 330 may be configured as a rotating structure, for example, a roller structure, so that the friction between the transmission belt 330 and the fixed tensioning wheel 503 can be reduced during movement of the transmission belt 330. The arrangement of the movable tensioning wheel 501 and the fixed tensioning wheel 503 ensures that unexpected slip does not occur when the driving wheel 321 performs power output on the transmission belt 330, thereby improving the control precision of the device in the present invention. It should be noted that the arrangement of the movable tensioning wheel 501 and the fixed tensioning wheel 503 is not necessary, and such arrangement may not be performed. In addition, the movable tensioning wheel 501 and the fixed tensioning wheel 503 do not need to appear at the same time.

Figure 8:
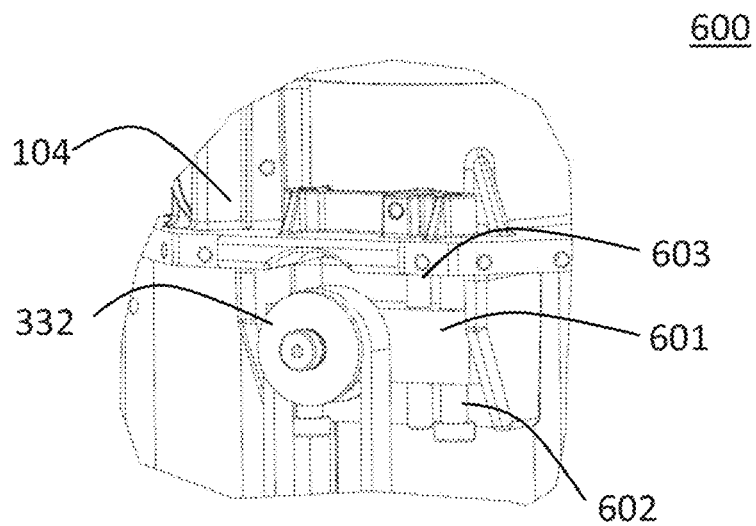
FIG. 8 is a schematic structural view of a driven wheel adjusting device according to some embodiments of the present invention.

As shown in FIG. 8, a schematic structural view of a driven wheel adjusting device 600 in some embodiments of the present invention is shown. The driven wheel adjusting device 600 can be used for adjusting the distance between the driven wheel 332 and the driving wheel 321. In some embodiments, the driven wheel 332 may be disposed on the frame 104 by means of the driven wheel adjusting device 600. The driven wheel adjusting device 600 may include a fixing seat 601, where the driven wheel 332 may be disposed on the fixing seat 601 by means of a rotating shaft or any other means. The driven wheel adjusting device 600 may further include an adjusting rod 602. In some embodiments, the adjusting rod 602 may be connected to the fixing seat 601 and the frame 104 by means of threads. For example, the adjusting rod 602 may be a screw including an external thread structure, while the fixing seat 601 and the frame 104 are both provided with an internal thread structure mated with the screw. The adjusting rod 602 can be adjusted to adjust relative positions of the fixing seat 601 and the frame 104, thereby driving the driven wheel 332 to move to achieve adjustment of the position of the driven wheel 332. The aforementioned adjustment can change the distance between the driven wheel 332 and the driving wheel 321, and further adjust the degree of attachment of the driving wheel 321 to the transmission belt 330. It should be noted that the number of the adjusting rods 602 in the driven wheel adjusting device 600 can be freely adjusted according to actual needs. In order to make the connection between the driven wheel adjusting device 600 and the frame 104 more smooth, in some embodiments, the driven wheel adjusting device 600 may further include a guide rod 603. One end of the guide rod 603 may be fixedly connected to the frame and the other end passes through the aforementioned fixing seat 601. Such arrangement ensures that when adjusting the position of the driven wheel 332, the driven wheel adjusting device 600 moves along the guide rod 603 and does not easily have unfavorable situations such as swinging. Moreover, after the adjustment of the position of the driven wheel 332 is completed, during use of the device, the guide rod 603 also enables more firm fixing of the driven wheel 332.

Figure 9:
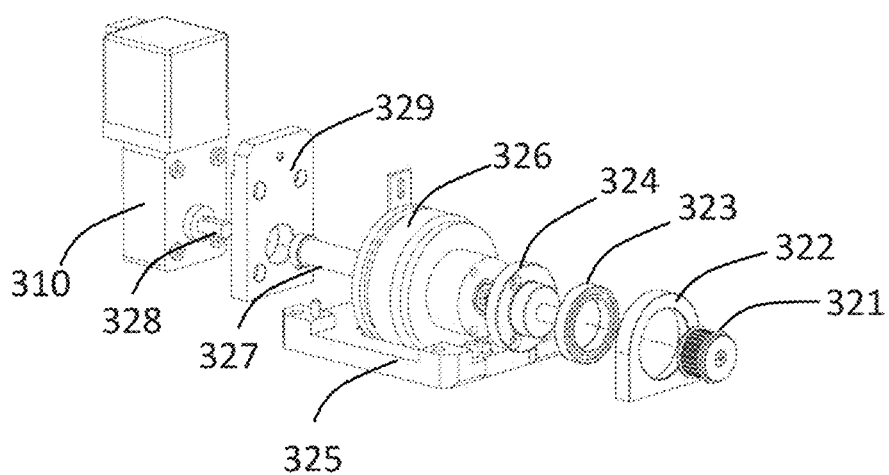
FIG. 9 is a schematic structural view of a clutch according to some embodiments of the present invention.

As shown in FIG. 9, a schematic structural view of the clutch 320 in some embodiments of the present invention is shown. The clutch 320 may be an electromagnetic clutch, and accordingly, includes a driving wheel 321, a bearing seat 322, a support bearing 323, an adapter 324, a base 325, and an electromagnetic clutch body 326. The electromagnetic clutch body 326 is disposed on the base 325 to achieve positioning thereof. The electromagnetic clutch body 326 is connected to the adapter 324, and the adapter 324 is rotatably connected to the support bearing 323. The support bearing 323 is disposed on the bearing seat 322, can provide support to the adapter 324, and does not affect the rotation of the adapter 324. The adapter 324 is connected to the driving wheel 321 through a rotating shaft. In this way, the electromagnetic clutch body 326 is rotatably connected to the driving wheel 321 through the adapter 324. In addition, the electromagnetic clutch body 326 is further provided with a shaft 327. The shaft 327 may cooperate with the output shaft 328 of the motor assembly 310 to achieve power output of the motor assembly 310. Referring to FIG. 3 and FIG. 9, in some embodiments, the motor assembly 310 may be connected to a fixing plate 329 and disposed on the base 325 by means of the fixing plate 329.

Figure 10:
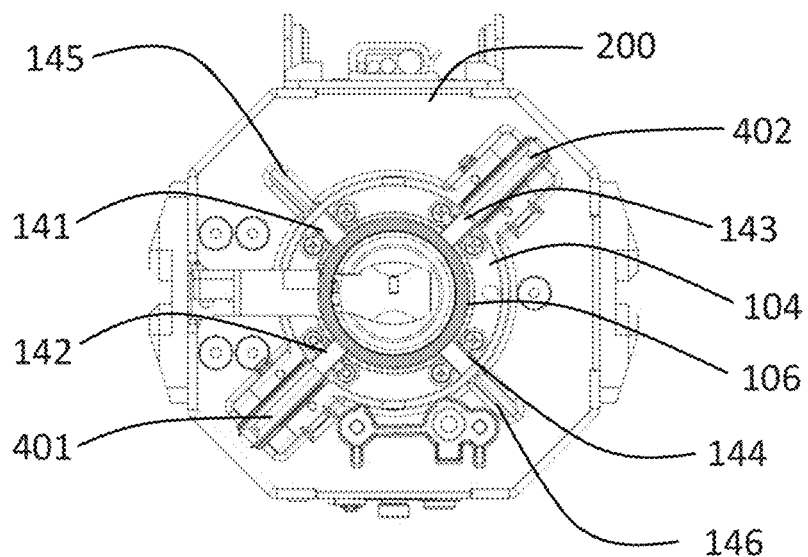
FIG. 10 is a schematic view illustrating connection relationships between a frame and the counterweight as well as the adjustable arm according to some embodiments of the present invention.

In order to further improve the smoothness of the counterweight 200 and the adjustable arm 106 during movement along the frame 104, a second pulley block and a third pulley block may be further provided. As shown in FIG. 10, a schematic view illustrating connection relationships between the frame 104 and the counterweight 200 as well as the adjustable arm 106 in some embodiments of the present invention is shown. In some embodiments, the frame 104 is provided with a number of pulleys, for example, pulleys 141 to 144, which together form the second pulley block. The second pulley block may be slidably connected to the adjustable arm 106 during movement of the adjustable arm 106, so as to reduce the friction between the frame 104 and the adjustable arm 106. Similarly, the counterweight 200 may also be provided with a number of pulley structures, such as pulleys 145 and 146, which together form the third pulley block. The third pulley block can achieve slidable connection between the counterweight 200 and the frame 104 to reduce the friction between them during movement of the counterweight 200. It should be noted that under the teachings of the present invention, the numbers and positions of the pulleys in the second pulley block and the third pulley block can be adjusted.

Figure 11:
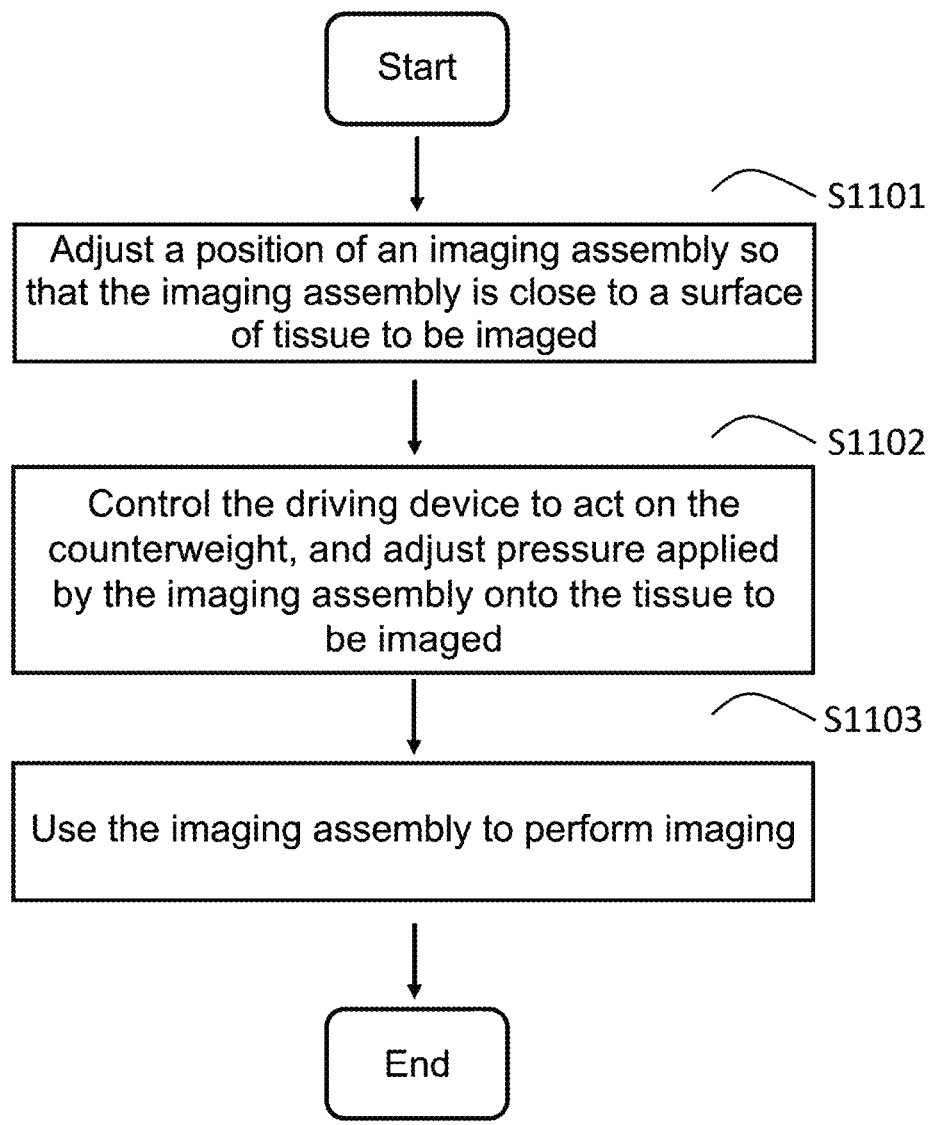
FIG. 11 is a flowchart of an imaging method according to some embodiments of the present invention.

As shown in FIG. 11, FIG. 11 is a flowchart of an imaging method of an imaging device in some embodiments of the present invention. The imaging method may be implemented by the imaging device in any of the embodiments described above. The imaging method of the imaging device in any of the embodiments of the present invention is now further described.

Step S1101: adjust a position of the imaging assembly 108 so that the imaging assembly is close to a surface of tissue to be imaged. According to the above description, in some embodiments, the weight of the counterweight 200 is specially designed and is approximately equal to the sum of the weights of the adjustable arm 106 and the imaging assembly 108. In this case, it will become easier for an operator to adjust the position of the imaging assembly 108. Since such setting ensures that the imaging assembly 108 is substantially neutrally buoyant, it is only needed to apply a small upward or downward force to the imaging assembly 108 to adjust the position thereof in the vertical direction, so that the imaging assembly 108 can be close to the surface of the tissue to be imaged to prepare for the next step imaging.

The pressure applied by the imaging assembly 108 onto the tissue to be imaged has an important impact on the imaging quality—an excessively large or small force is disadvantageous to improving the imaging quality, and therefore adjustment needs to be made before imaging. Step S1102: control the driving device 301 to act on the counterweight 200, and adjust pressure applied by the imaging assembly 108 onto the tissue to be imaged. In some cases, the pressure of the imaging assembly 108 on the tissue to be imaged may need to be increased; at this time, the driving device 301 can be controlled to act on the counterweight 200, for example, to apply to the counterweight 200 a force that is upward relative to the bottom of the frame 104. In this case, the force applied by the counterweight 200 to the bottom of the adjustable arm 106 through the cable will be decreased. Then, due to the gravity of the adjustable arm 106 and the imaging assembly 108, the imaging assembly 108 will have a tendency to move downward; at this time, the pressure of the imaging assembly 108 on the tissue to be imaged will be increased. On the contrary, in some other cases, the pressure of the imaging assembly 108 on the tissue to be imaged may need to be decreased; at this time, the driving device 301 can be controlled to act on the counterweight 200, and apply to the counterweight 200 a force that is downward relative to the bottom of the frame 104. In this case, the force applied by the counterweight 200 to the bottom of the adjustable arm 106 through the cable will be increased. Because of the force, the pressure of the imaging assembly 108 on the tissue to be imaged will be decreased. The effect of the driving device 301 on the counterweight 200 is controlled, so that the operator can easily adjust the pressure applied by the imaging assembly 108 onto the tissue to be imaged.

After step S1102, the operator adjusts the pressure applied by the imaging assembly 108 onto the tissue to be imaged to a certain degree, and then the imaging assembly 108 can be used to perform imaging, as in step S1103 of FIG. 11. In some embodiments, the imaging assembly 108 includes an ultrasonic transducer, and the imaging assembly 108 may be used to ultrasonically image the tissue to be imaged. The specific imaging process will not be described herein again. However, it should be noted that the order of operation of the aforementioned steps may be adjusted. Moreover, the operator may alternately perform the aforementioned steps according to actual needs. For example, in the imaging process, the imaging quality may be changed for some reasons; at this time, the operator may select to adjust the pressure applied by the imaging assembly again.

As described above, in some embodiments, the driving device 301 includes a clutch 320. When step S1101 is performed, the clutch 320 may be in a disengaged state; at this time, the driving device 301 will not act on the transmission belt 330, and accordingly, the transmission belt 330 has small resistance only to the counterweight 200. At this time, the operator can conveniently, manually, and rapidly operate the adjustable arm 106 or the imaging assembly 108 to bring the imaging assembly 108 close to the surface of the tissue to be imaged. It should be noted that the operator may also select to adjust the clutch to an engaged state and achieve adjustment of the position of the imaging assembly 108 using the actuation of the driving device 301.

In addition, when step S1102 is performed, the clutch 320 may be in an engaged state; at this time, the driving device 301 can act on the transmission belt 330 and then act on the counterweight 200 through the transmission belt 330, so as to change the force applied by the counterweight 200 to the adjustable arm 106. The change of the force results in a change in the force applied to the imaging assembly 108, and then changes the pressure applied by the imaging assembly 108 onto the tissue to be imaged.

The purpose of providing the above specific embodiments is to allow the content disclosed in the present invention to be understood more thoroughly and comprehensively, but the present invention is not limited to these specific embodiments. Those skilled in the art should understand that various modifications, equivalent replacements, and changes can also be made to the present invention. As long as these changes do not violate the spirit of the present invention, they should be included in the scope of protection of the present invention.

The invention claimed is:

1. An ultrasonic imaging device, comprising:
    an imaging assembly, the imaging assembly comprising an ultrasonic transducer for imaging tissue to be imaged;
    an adjustable arm, wherein one end of the adjustable arm is connected to the imaging assembly;
    a counterweight, the counterweight being connected to the other end of the adjustable arm through a cable;
    a frame, the frame being capable of guiding movement when the counterweight and/or adjustable arm moves; and
    a transmission assembly, the transmission assembly comprising a driving device and a transmission belt, wherein the driving device is connected to the transmission belt, and the transmission belt is connected to the counterweight; the driving device is capable of acting on the counterweight through the transmission belt, so as to adjust pressure applied by the imaging assembly onto the tissue to be imaged,
    wherein the driving device comprises a motor assembly and a clutch, the motor assembly is connected to the clutch, and the clutch is connected to the transmission belt,
    wherein the motor assembly comprises a motor and a reducer; an output shaft of the motor comprises a worm structure; the reducer comprises a worm gear mated with the worm structure; the worm is mated with the worm gear to enable automatic locking of a position of the counterweight in an OFF state of the motor, and
    wherein, when the pressure applied by the imaging assembly onto the tissue is adjusted to an expected value, the position of the counterweight is automatically locked by the motor being toggled to the OFF state.

2. The device according to claim 1, further comprising a first pulley block, wherein the first pulley block comprises a number of pulleys disposed on the frame and the other end of the adjustable arm; the cable is wound through the pulley block and has two ends disposed on the counterweight.

3. The device according to claim 1, wherein the frame comprises a number of pillar structures, and the counterweight is provided with through-holes for the pillar structures to pass through; the pillar structures are usable for guiding movement during movement of the counterweight.

4. The device according to claim 1, wherein the frame comprises a hollow structure, and at least part of the adjustable arm is disposed in the hollow structure; the hollow structure is usable for guiding movement during movement of the adjustable arm.

5. The device according to claim 5claim 1, wherein the clutch is connected to the transmission belt through a driving wheel.

6. The device according to claim 5, further comprising a driven wheel, wherein the driven wheel is disposed on the frame and connected to the transmission belt.

7. The device according to claim 6, further comprising a driven wheel adjusting device, wherein the driven wheel is disposed on the frame by means of the driven wheel adjusting device; the driven wheel adjusting device comprises a fixing seat and an adjusting rod;

the driven wheel is disposed on the fixing seat; the adjusting rod is threadedly connected to the fixing seat and the frame, so that a position of the driven wheel is capable of being adjusted by rotating the adjusting rod.

8. The device according to claim 7, wherein the driven wheel adjusting device further comprises a guide rod, one end of the guide rod is disposed on the frame, and the other end passes through the fixing seat.

9. The device according to claim 5, wherein the driving wheel comprises a gear structure, and a portion of the transmission belt in contact with the driving wheel has a tooth-like structure that is engaged with the gear structure.

10. The device according to claim 5, further comprising a tensioning device, wherein the tensioning device comprises a movable tensioning wheel; the movable tensioning wheel is disposed on the frame and movably attached to the transmission belt through a torsion spring.

11. The device according to claim 10, wherein the tensioning device further comprises a fixed tensioning wheel, and the fixed tensioning wheel is disposed opposite to the movable tensioning wheel and attached to the transmission belt.

12. The device according to claim 1, wherein one side of the transmission belt is connected to the counterweight to drive the counterweight to move.

13. The device according to claim 1, wherein the clutch comprises an electromagnetic clutch body, a base, an adapter, a support bearing, a bearing seat, and a driving wheel; the electromagnetic clutch body is disposed on the base and connected to the adapter; the adapter is rotatably connected to the support bearing and is connected to the driving wheel through a rotating shaft; the support bearing is disposed on the bearing seat; the driving wheel is connected to the transmission belt.

14. The device according to claim 1, further comprising a second pulley block disposed on the frame and a third pulley block disposed on the counterweight; the second pulley block is used for sliding connection between the frame and the adjustable arm; the third pulley block is used for sliding connection between the frame and the counterweight.

15. An imaging method using the device according to claim 1, comprising:

adjusting a position of an imaging assembly so that the imaging assembly is close to a surface of tissue to be imaged;

controlling the driving device to act on the counterweight, and adjusting pressure applied by the imaging assembly onto the tissue to be imaged; and using the imaging assembly to perform imaging.

16. The method according to claim 15, wherein when the position of the imaging assembly is adjusted, the clutch in the driving device is in a disengaged state; at this time, the position of the imaging assembly is adjusted manually.

17. The method according to claim 15, wherein when the driving device acts on the counterweight, the clutch in the driving device is in an engaged state; at this time, the driving device is capable of acting on the counterweight to change a force applied by the counterweight to the adjustable arm, thereby changing a force applied to the imaging assembly.

* * * * *